(12) United States Patent
Lian et al.

(10) Patent No.: US 7,835,792 B2
(45) Date of Patent: Nov. 16, 2010

(54) IMPLANTABLE CARDIAC DEVICE

(75) Inventors: Jie Lian, Beaverton, OR (US); Dirk Muessig, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 635 days.

(21) Appl. No.: 11/742,377

(22) Filed: Apr. 30, 2007

(65) Prior Publication Data

US 2008/0269826 A1 Oct. 30, 2008

(51) Int. Cl.
*A61N 1/365* (2006.01)
(52) U.S. Cl. ...................................... 607/17
(58) Field of Classification Search ............ 607/9, 607/17, 18, 19, 27
See application file for complete search history.

(56) References Cited

U.S. PATENT DOCUMENTS

| | | | |
|---|---|---|---|
| 4,303,075 A | 12/1981 | Heilman et al. | |
| 5,300,092 A | 4/1994 | Schaldach | |
| 5,309,919 A * | 5/1994 | Snell et al. | 600/510 |
| 5,350,408 A | 9/1994 | Schaldach | |
| 5,441,522 A * | 8/1995 | Schuller | 607/9 |
| 5,476,483 A * | 12/1995 | Bornzin et al. | 607/17 |
| 5,645,576 A | 7/1997 | Limousin et al. | |
| 5,733,312 A | 3/1998 | Schloss et al. | |
| 5,814,087 A | 9/1998 | Renirie | |
| 5,861,011 A | 1/1999 | Stoop | |
| 6,128,534 A * | 10/2000 | Park et al. | 607/17 |
| 6,519,494 B1 | 2/2003 | Hutten | |
| 6,773,404 B2 | 8/2004 | Poezevera et al. | |
| 6,973,350 B1 * | 12/2005 | Levine et al. | 607/27 |
| 2005/0131469 A1 | 6/2005 | Cohen | |

* cited by examiner

*Primary Examiner*—Niketa I Patel
*Assistant Examiner*—Hiba El-Kaissi
(74) *Attorney, Agent, or Firm*—ARC IP Law, PC; Joseph J. Mayo

(57) ABSTRACT

A heart stimulator is adapted to adapt an atrioventricular delay interval or an interventricular delay interval or both during night time by adding a delay interval to a respective daytime interval, and the device statistics for day and night are calculated, stored, and can be displayed separately.

12 Claims, 2 Drawing Sheets

IMPLANTABLE CARDIAC DEVICE

BACKGROUND OF THE INVENTION

1. Field of the Invention

The invention relates to implantable cardiac devices in general and to implantable heart stimulators such as cardiac pacemakers, implantable cardioverter/defibrillators (ICDs) or a combination thereof in particular.

2. Description of the Related Art

Heart stimulators such as implantable pacemakers can be used for treating a plurality of different malfunctions of a heart. Many pacemakers are designed to treat the right chambers of a heart, the right atrium and the right ventricle, only.

In such case, also the delay between a right atrial contraction and a right ventricular contraction needs to be optimized in order to properly synchronize right and left ventricular contraction and the right atrial contraction. The delay interval between a right atrial contraction and the right ventricular contraction usually is called atrioventricular delay interval that is abbreviated AVD.

Biventricular pacemakers are able to pace both ventricles of a heart.

Biventricular pacemakers are used for a cardiac re-synchronization therapy that shall synchronize right ventricular contraction and left ventricular contraction to improve the output of a heart exhibiting a cardiovascular disease. In particular, cardiac synchronization therapy is used to treat heart failure in patients with wide QRS complex that results from a delayed excitation of the left heart side. It is believed, that a main contributor to heart failure (the heart's inability to generate enough cardiac output) is an asynchronous mechanical contraction of the left and right side of the heart.

In order to restore an optimum cardiac output by proper synchronization of consecutive contractions of the chambers of a heart, the duration of a delay interval between a right ventricular contraction and a left ventricular contraction also needs to be optimized. This delay interval is called interventricular delay or interventricular delay interval or interventricular interval and often times is abbreviated VVD.

Furthermore, in order to restore an optimal cardiac output the proper sequence of the contractions of the chambers of a heart needs to be optimized. Positive values of the VVD denote that the rightventricular chamber is stimulated first and after the VVD the leftventricular. Negative values of the VVD denote that the leftventricular chamber is stimulated first, followed by the right ventricular chamber after the VVD.

US 2005/0131469 discloses a hemodynamic optimization system that automatically adjusts atrioventricular delay and the interventricular delay until maximum hemodynamic output is achieved. According to US 2005/0131469 hemodynamic information can be gathered via impedance measures, QT-interval, accelerometer, mixed venous oxygen duration, cardiac output or similar marker, intracardiac pressure monitoring, blood pressure, temperature and other suitable physiologic parameters. According to U.S. Pat. No. 4,303,075 the atrial ventricular delay is optimized until stroke volume reaches a maximum. Stroke volume is measured by way of an impedance processor for determining a peak to peak amplitude that corresponds to the stroke volume of the heart.

Depending on the mode of operation of the heart stimulator, triggering and delivery of stimulation pulses is inhibited if a natural contraction of a respective heart chamber is sensed prior to expiration of a respective delay interval. Thus, stimulation pulses are only triggered if needed. Such mode of operation is called demand mode.

Another aspect of state of the art heart stimulators is called demand pacing. In a demand pacing mode a stimulation pulse only is delivered when no natural (intrinsic) contraction of a respective heart chamber occurs during a preset interval. Stimulation of a heart chamber causing a so called paced event is inhibited if a natural contraction of that heart chamber, called sense event, is sensed prior to expiration of a respective interval, e.g. AVD or VVD. A contraction of a heart chamber, either stimulated (pace event) or intrinsic (sense event), is called event. Stimulation of a heart chamber is also called pacing a heart chamber.

In such demand mode, a heart stimulator puts out an electrical stimulation pulse to a heart chamber at time out of a respective delay interval unless a sense event occurs prior to expiration of a respective delay interval. In particular, a stimulation pulse to the right ventricle is triggered and delivered at the end of the atrioventricular delay interval if no natural right ventricular contraction is sensed prior to expiration of the atrioventricular delay interval. Similarly, a stimulation pulse to the left ventricle is triggered and delivered if no left ventricular contraction is sensed prior to expiration of the interventricular delay interval.

In order to be able to operate in a demand mode, a heart stimulator comprises sensing stages for sensing natural (also called intrinsic) contractions of a respective heart chamber. A natural contraction of a heart chamber is also called an intrinsic event (or "sensed event" since it only becomes relevant if such intrinsic event is actually sensed) in contrast to a contraction of a heart chamber due to stimulation that is called a paced event. For each heart chamber to be stimulated, e.g. right atrium, right ventricle and left ventricle, a separate sensing channel (including sensing stages) is provided in order to discriminate between intrinsic events of different origin. Atrial events are usually designated with A and ventricular events are designated with V since the atrioventricular delay is the delay between an atrial event and a ventricular event it is abbreviated AVD.

Another parameter to be controlled by a heart stimulator is the heart rate. Usually, a base rate is set that determines a minimum heart rate that is enforced by the heart stimulator if the base rate is not met or exceeded by the natural, intrinsic heart rate of the heart.

Setting of the base (or basic) rate may differ between day and night in order to meet the natural circadian variations in a heart cycle.

Most current implant devices allow programming of the night basic rate. The start and end time of the night phase can be empirically set through programming the implant device. On the other hand, different methods have been proposed to allow the implant device to automatically detect the day and night phases, for example, by analyzing the signals measured by activity sensor (U.S. Pat. No. 5,300,092 and U.S. Pat. No. 5,350,408), by analyzing the activity variance provided by the activity sensor (U.S. Pat. No. 5,476,483, and U.S. Pat. No. 6,128,534), by analyzing both activity sensor signal and the cardiac rhythm information (U.S. Pat. No. 5,645,576), by analyzing the QT intervals (U.S. Pat. No. 5,861,011), by analyzing the blood temperature (U.S. Pat. No. 5,814,087), or by analyzing the impedance-based respiration signals (U.S. Pat. No. 6,519,494 and U.S. Pat. No. 6,773,404). In addition, the method for day-night transition of pacing rate was also disclosed (U.S. Pat. No. 5,733,312).

The following lists the most relevant patents found and considered by the inventors:

| Pat/Appl. No. | Issued Date | Inventors | Assignee |
| --- | --- | --- | --- |
| U.S. Pat. No. 5,300,092 | April, 1994 | Schaldach | Biotronik |
| U.S. Pat. No. 5,350,408 | September, 1994 | Schaldach | Biotronik |
| U.S. Pat. No. 5,476,483 | December, 1995 | Bornzin et al. | Pacesetter |
| U.S. Pat. No. 5,645,576 | July, 1997 | Limousin et al. | ELA |
| U.S. Pat. No. 5,733,312 | March, 1998 | Schloss et al. | Pacesetter |
| U.S. Pat. No. 5,814,087 | September, 1998 | Renirie | Medtronic |
| U.S. Pat. No. 5,861,011 | January, 1999 | Stoop | Vitatron |
| U.S. Pat. No. 6,128,534 | October, 2000 | Park et al. | Pacesetter |
| U.S. Pat. No. 6,519,494 | February, 2003 | Hutten | Biotronik |
| U.S. Pat. No. 6,773,404 | August, 2004 | Poezevera et al. | ELA |

Yet another commonly known aspect of modern heart stimulators concerns an aspect called hysteresis. Hysteresis is applied to promote intrinsic contractions of a heart chamber, e.g. the right ventricle by prolonging an AVD by a hysteresis interval after a natural contraction of said heart chamber was sensed thus increasing the likelihood that another natural contraction of said heart chamber falls into the prolonged AVD. Only if no intrinsic contraction of the heart chamber is sensed during the prolonged AVD, the heart stimulator switches back to the regular (non hysteresis) AVD.

Besides the heart rate, other cardiac electrophysiological properties also show certain circadian patterns.

The AV node is innervated by both sympathetic and vagal fibers. The AV nodal conduction time is shortened as sympathetic tone increases, or lengthened as vagal tone increases. It is well known that a person's vagal tone is enhanced during sleep, resulting in prolonged AV conduction time at night.

On the other hand, for three-chamber cardiac resynchronization therapy (CRT) devices that deliver bi-ventricular paces to synchronize the left and right ventricular contractions, the VV delay must be optimized. It is known that the optimal VV delay has substantial inter-subject variability. In addition, for each individual patient, the optimal VV delay also varies based on the heart rate or activity level. Therefore, the circadian variation of the optimal VV delay is also expected.

Therefore, there is a need for the implant device can automatically adjust the device AV delay and VV delay for day and night, respectively.

Yet another limitation common to all existing implant devices is that the device measures and maintains daily (day and night) lumped statistics, thus cannot reveal the potential circadian pattern of cardiac electrophysiological behaviors. Therefore, there is a need for the implant device to measure and maintain the device statistics for day and night independently, thus potentially yielding more diagnostic information.

For the purpose of this disclosure, the following abbreviations are used are used:

| Abbreviation | Meaning |
| --- | --- |
| ACC | Automatic Capture Control |
| Ap, AP | Atrial pace (stimulation) event |
| Ars | refractory atrial sense event |
| As, AS | Atrial sense event |
| A | Any atrial event |
| AES | Atrial extra systole |
| AF | Atrial fibrillation |
| AT | Atrial tachycardia |
| ATP | Anti tachycardia pacing |
| ATT | Automatic threshold tracking |
| AV | atrioventricular |
| AVD | AV delay as applied by the pacemaker (in contrast to intrinsic AV delay) |
| ΔAVD | Offset AVD |
| CRT | cardiac resynchronization therapy |
| D | Intra cycle delay interval (AVD or VVD) |
| ΔD | Offset interval |
| LVp | Left ventricular stimulation pulse |
| PMT | Pacemaker mediated tachycardia |
| PVARP | Post-ventricular atrial refractory period |
| RA | Right atrial event |
| RV | Right ventricular event |
| RVp | Right ventricular pace event |
| VES | Ventricular extra-systole |
| Vp, VP | Ventricular pace (stimulation) event |
| Vs, VS | Ventricular sense event |
| Vrs | Ventricular refractory sense event |
| V | Any ventricular event |
| VF | ventricular fibrillation |
| VT | ventricular tachycardia |
| VVD | Interventricular delay interval |
| ΔVVD | Offset VVD |

SUMMARY OF THE INVENTION

The object to be solved by the present invention is to provide for a device and a method for optimal synchronization of contractions of different heart chambers.

For the purpose of this disclosure, the atrioventricular delay (AVD) and the interventricular delay (VVD) are commonly designated intra cycle delay intervals since the atrioventricular delay interval and the interventricular delay interval determine the timing within one heart cycle whereas intervals such the intervals between consecutive (right) ventricular events or atrial events, respectively, determine a stimulation rate and thus the timing from one (paced) heart cycle to another.

According to the present invention the afore mentioned object is solved by a heart stimulator for pacing of a heart that comprises at least one stimulation pulse generator that is connected to or can be connected to stimulation electrode leads for stimulating at least two different chambers of the heart. The stimulation pulse generator is adapted to generate stimulation pulses for pacing an individual heart chamber when triggered: The heart stimulator further comprises a control unit that is connected to the stimulation pulse generator and that is adapted to trigger stimulation pulses for an individual heart chamber such that a stimulation of a next heart chamber occurs when an intra heart cycle delay interval started by natural or a stimulated contraction of a previous heart chamber expires. The intra heart cycle delay interval $D_{night}$ during nighttime differs from the corresponding intra heart cycle delay interval $D_{day}$ to be applied during day time by a preset difference interval $\Delta D$:

$$D_{night} = D_{day} + \Delta D$$

Preferably the heart stimulator comprises different stimulation pulse generators for the different heart chambers to be eventually stimulated. In one preferred embodiment, the hear stimulator comprises a right atrial stimulation pulse generator and a right ventricular stimulation pulse generator that can be triggered separately by said control unit. In this embodiment the intra heart cycle delay interval is an atrioventricular interval AVD that is started by a right atrial event RA and that schedules a right ventricular stimulation pulse RVp to be delivered at expiration of said AVD unless inhibited. The control unit is adapted to apply a daytime $AVD_{day}$ at daytime and a nighttime $AVD_{night}$ at night that differ from each other by an offset interval $\Delta AVD$ as follows:

$$AVD_{night}=AVD_{day}+\Delta AVD$$

In another preferred embodiment that can be combined with the first preferred embodiment the heart stimulator comprises a right ventricular stimulation pulse generator and a left ventricular stimulation pulse generator that can be triggered separately by said control unit. In this embodiment the intra heart cycle delay interval is an interventricular interval VVD that is started by a right ventricular event RV and that schedules a left ventricular stimulation pulse LVp to be delivered at expiration of said VVD unless inhibited. The control unit is adapted to apply a daytime $VVD_{day}$ at daytime and a nighttime $VVD_{night}$ at night that differ from each other by an offset interval $\Delta VVD$ as follows:

$$VVD_{night}=VVD_{day}+\Delta VVD$$

Another aspect of the invention concerns a method of adapting an atrioventricular delay interval (AVD) or an interventricular delay interval (VVD) or both for scheduling right ventricular or left ventricular stimulation or both, said method comprising the steps of:

Setting a daytime intra cycle delay interval $D_{day}$

Applying said daytime intra cycle delay interval $D_{day}$ during daytime

Applying a night time intra cycle delay interval $D_{night}$ during night time, wherein said nighttime delay interval $D_{night}$ corresponds to said daytime intra cycle delay interval $D_{day}$ plus an offset interval $\Delta D$:

$$D_{night}=D_{day}+DD$$

The invention is based on the insight that the aspect of adapting AVD and VVD has not been adequately addressed in the prior art. Although U.S. Pat. No. 5,733,312 and U.S. Pat. No. 6,128,534 propose to separate programming a plural of device parameters for day and night, including the AVD, all disclosed embodiments were for the programming of basic rate, and there is no description or suggestion on how AVD should be programmed for the night. Regarding the VVD, there is no prior art on separate programming of VVD for day and night. Finally, there is no day/night separation of the device statistics, which may provide important diagnostic information.

A preferred value of the $\Delta AVD$ is between 0 ms and 100 ms, preferably around 20 ms. Thus, $\Delta AVD$ is never a negative value.

A preferred offset $\Delta VVD$ is between −50 ms and +50 ms taking into account that VVD itself may be a negative value. A preferred default value would be 0 ms, that is, a dedicated $\Delta VVD$ value that can be altered is stored in the heart stimulator and is used whenever applicable. Thus a biventricular heart stimulator operating a $\Delta VVD$ (or a $\Delta AVD$) of 0 ms differs from a heart stimulator that does not provide for the flexibility to apply different delay intervals during daytime and during night time although the behavior may be the same.

In a further preferred embodiment, the nighttime adaptation of AVD is combined with other heart stimulator features involving the AVD, as follows:

The heart stimulator or its control unit, respectively, may be adapted to apply different AVDs depending on whether the event starting the AVD is a sense event or a pace event and thus to apply a sensed AVD and paced AVD with programmed sense compensation. In such heart stimulator the night AVD is also separated for the atrial sense and atrial pace. That is, the nighttime sense $AVD_{night}$ is the daytime sense $AVD_{day}$ plus $\Delta AVD$, and the nighttime pace $AVD_{night}$ is the daytime pace $AVD_{day}$ plus $\Delta AVD$.

In a heart stimulator that provides for a dynamic AVD that adjusts with the heart rate, the nighttime $AVD_{night}$ is the sum of the daytime dynamic $AVD_{day}$ (that varies with heart rate) and $\Delta AVD$, thus also adjusting with the heart rate.

In a heart stimulator that provides for an AV hysteresis feature that periodically searches for the intrinsic AV conduction by switching between a short AVD and a long (hysteresis) AVD, the nighttime $AVD_{night}$ also has hysteresis behavior, by adding $\Delta AVD$ to the short AVD and long AVD, respectively.

If the heart stimulator according to a preferred embodiment provides for VP suppression feature that switches between VP suppression state wherein ventricular stimulation pulses (VP) are suppressed (long AVD and zero-energy VP) (see co-pending application U.S. patent application Ser. No. 11/484,336, filed on 10 Jul. 2006, incorporated herein by reference) and the VS alert state (periodic search for ventricular sense events VS), the nighttime $AVD_{night}$ is also adapted by adding $\Delta AVD$ to the $AVD_{day}$ settings in all operating states.

A parameter to be set in a heart stimulator not yet discussed herein is stimulation pulse strength. Although stimulation pulse strength is not of particular relevance for this invention, features for automatic determination and control of (sufficient) pulse strength can be combined with the inventive concept in preferred embodiments.

In order to cause effective excitation of a heart chamber to be stimulated, the stimulation pulse delivered to said heart chamber needs to be strong enough to cause such excitation, or, in other words, to cause capture of the heart chamber that is stimulated. Therefore, the stimulation pulse needs to have a strength above a stimulation threshold (or excitation threshold) of the heart chamber to be stimulated. On the other hand, a stimulation pulse having a strength that is much higher than the stimulation threshold would use more energy than necessary. In view of limited energy resources in an implantable medical device (IMD), unnecessary waste of energy is to be avoided to reduce battery depletion to a minimum. Therefore, modern implantable medical devices provide for automatic threshold control that continuously or periodically and automatically determines optimal stimulation pulse strength just above the stimulation threshold of a respective heart chamber. Further, periodically a heart stimulator may conduct an automatic threshold test (ATT) for automatically searching stimulation pulse strength that is sufficient to ensure reliable capture.

According to a preferred embodiment of the invention nighttime adaptation of AVD and, if applicable of VVD, is inhibited in certain operation modes including specially designed short AVD settings, for example, during the right ventricle automatic capture control (RV-ACC), or during the rhythm-based automatic right atrial threshold tracking (RA-ATT), or when a negative AV hysteresis is activated, the nighttime $AVD_{night}$ preferably does not add $\Delta AVD$ to the daytime $AVD_{day}$ value.

Also according to this invention, for CRT devices (biventricular heart stimulators), the nighttime $VVD_{night}$ is adapted to the daytime $VVD_{day}$ by adding a programmable offset $\Delta VVD$ as pointed out above. In a typical embodiment, the offset $\Delta VVD$ ranges from −50 ms to +50 ms, with default value 0 ms. Because both positive and negative $\Delta VVD$ can be programmed, the bi-ventricular activation sequence can be adjusted toward either right or left chamber. In other words, the daytime $VVD_{day}$ can be either increased or decreased during nighttime based on the programming of $\Delta VVD$.

In one embodiment, the start time and end time of the night are programmed through a user-interface in the external programming device, which can interrogate and program the implant device through the bi-directional telemetry.

In another embodiment, the rest (nighttime) and active (daytime) phases can be automatically determined based on analysis of the signal measured by activity sensor or based on the analysis of the respiration signal measured by impedance sensor.

In both cases it is preferred if the control unit is connected to a clock and a memory that contains data defining daytime and nighttime with respect to said clock, and the control unit adapts the AVD according to the data contained in the memory and an output signal of the clock.

Another feature of a preferred heart stimulator is that the heart stimulator collects data relating to different events to set up statistics are separately calculated and presented for day and night. This feature can be realized both, independently and in combination with the above mentioned intra cycle delay interval features.

Such device statistics, as known in the art, include but are not limited to:
- event sequence counters (AS-VS, AS-VP, AP-VS, AP-VP)
- ectopic event counters (AES, VES, etc.)
- unused event counters (Ars in PVARP, far-field As, Vrs, etc.)
- detection counters (AT/AF, VT/VF, PMT, VES lock in, 2:1 lock in, etc.)
- therapy counters (mode switch, ATP, cardioversion/defibrillation, etc.)
- trend histograms (A/V rate, A/V amplitude, impedance, activity sensor, etc.)
- pacing parameters (VP percentage, AP/VP amplitude, atrial/ventricle threshold, etc.)
- measured or derived diagnostic parameters (heart rate variability, body temperature, blood pressure, transthoracic impedance, etc.)
- and others.

In an exemplary embodiment, the counters are calculated and presented for day and night, respectively, and their sums are also given (day counter plus night counter). Preferably, the histograms are displayed in stacked bar graph format, so that not only the overall statistics, but also the day/night contributions to the statistics are available. In another embodiment, the programmer by default shows the daily (day and night) statistics after interrogating the device. A graphical user interface is provided to allow the user to switch to separate day/night statistics or toggle between day and night statistics.

It is believed by the inventors that by separating the day/night device statistics, the implant device can provide more diagnostic information, and may provide feedback on how to optimize the night AVD and night VVD. For example, separate presentation of the percentage of VP for day/night can facilitate adjusting ΔAVD and ΔVVD, to optimize the AVD and VVD for day and night. Also, separate presentation of the statistic information can potentially reveal circadian patterns, for example, arrhythmia episode, pacing threshold, etc., that otherwise would not be recognized based on daily (day and night) lumped statistics. Therefore, the separate day/night statistics can provide enhanced diagnostic information, which can be used to guide improved therapy.

Although the present invention is neither directed to technical details of event detection and discrimination (e.g. details of the sensing stage and the processing of signals generated by the sensing stage) nor to details of automatic capture control such features in general are incorporated in a preferred heart stimulator according to the invention. A number of solutions for intrinsic event detection and processing and for automatic capture control are unknown to the man skilled in the art.

It is to be appreciated that features of preferred embodiments of the invention may be combined in any useful manner thus arriving at further preferred embodiments of the invention not explicitly mentioned in this disclosure.

BRIEF DESCRIPTION OF THE DRAWINGS

The foregoing and other objects, advantages and novel features of the present invention can be understood and appreciated by reference to the following detailed description of the invention, taken in conjunction the accompanying drawings, in which.

DETAILED DESCRIPTION OF THE INVENTION

Figure 1:
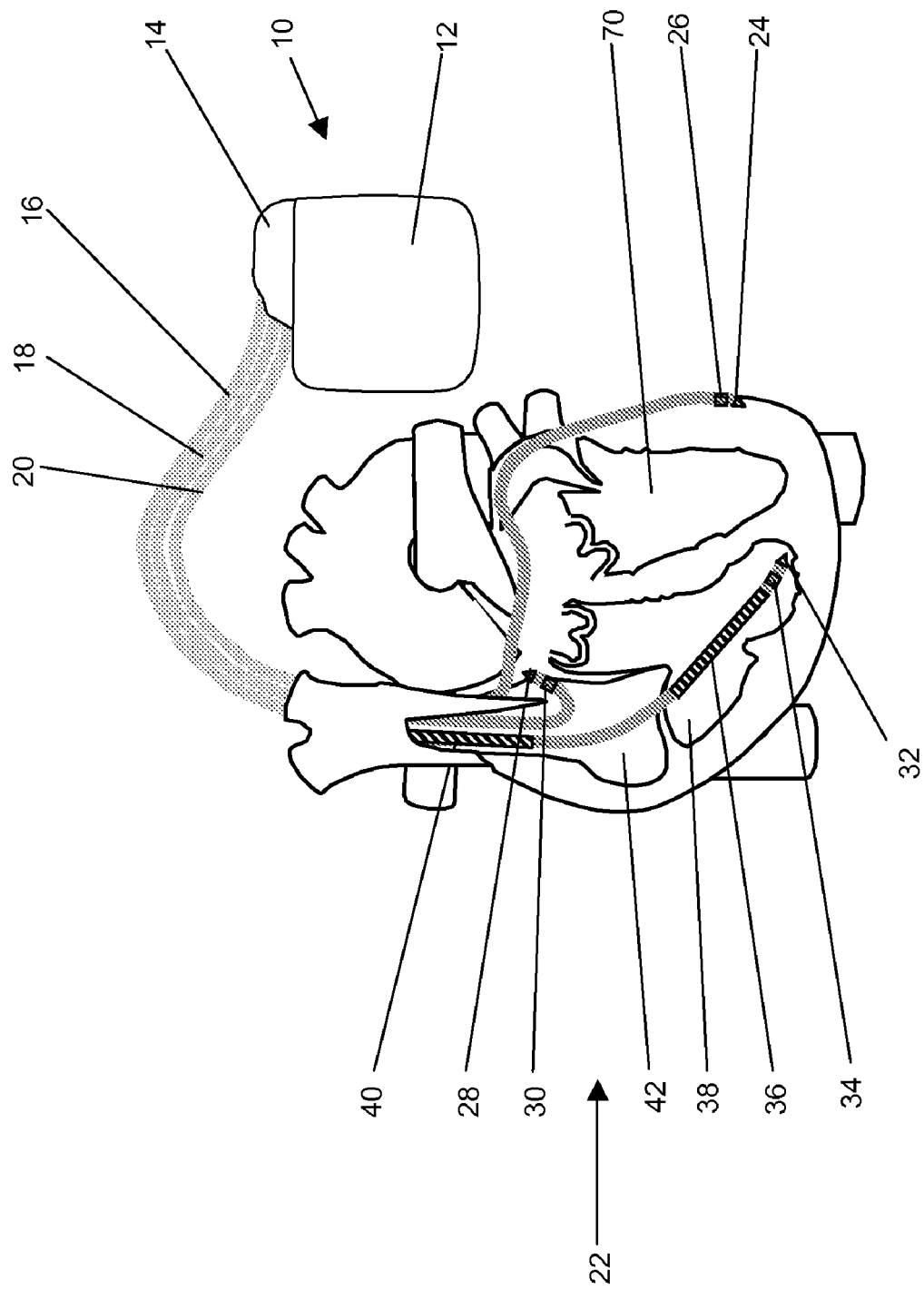
FIG. 1 illustrates the heart stimulator connected to electrode leads that are placed in a heart.

FIG. 1 shows that stimulator 10 comprises a case 12 and header 14.

The heart stimulator 10 is connected to three electrode leads, namely a right ventricular electrode lead for 16, a right atrial electrode lead 18 and a left ventricular electrode lead 20.

The left ventricular electrode lead 20 is designed to pass trough the coronary sinus of heart 22. A typical electrode suitable for use with heart stimulator 10 is the electrode lead Corox+ UP/BB by the applicant. Left ventricular electrode lead 20 comprises a left ventricular tip electrode 24 at the distal end of left ventricular electrode lead 20 and a left ventricular ring electrode 26.

Atrial electrode lead 18 comprises a right atrial tip electrode 28 at the distal end of right atrial electrode lead 18 and a right atrial ring electrode 30.

The right ventricular electrode lead 16 comprises right ventricular tip electrode 32 at the distal end of right ventricular electrode lead 16 and a right ventricular ring electrode 34.

In order to illustrate that heart stimulator 10 may be adapted to act as an implantable cardioverter/defibrillator (ICD) ventricular electrode lead 16 also exhibits a ventricular shock coil 36 for the delivery of defibrillation shocks to right ventricle 38 of heart 22 and an atrial shock coil 40 for the delivery of atrial defibrillation shocks to a right atrium 42 of heart 22.

Each electrode and shock coil of electrode leads 16 to 20 is separately connected to an electric circuit enclosed by case 12 of heart stimulator 10 by way of electrical contacts of a plug (not shown) at the proximal end of each electrode lead 16 to 20 and corresponding contacts (not shown) in header 14 of heart stimulator 10.

Figure 2:
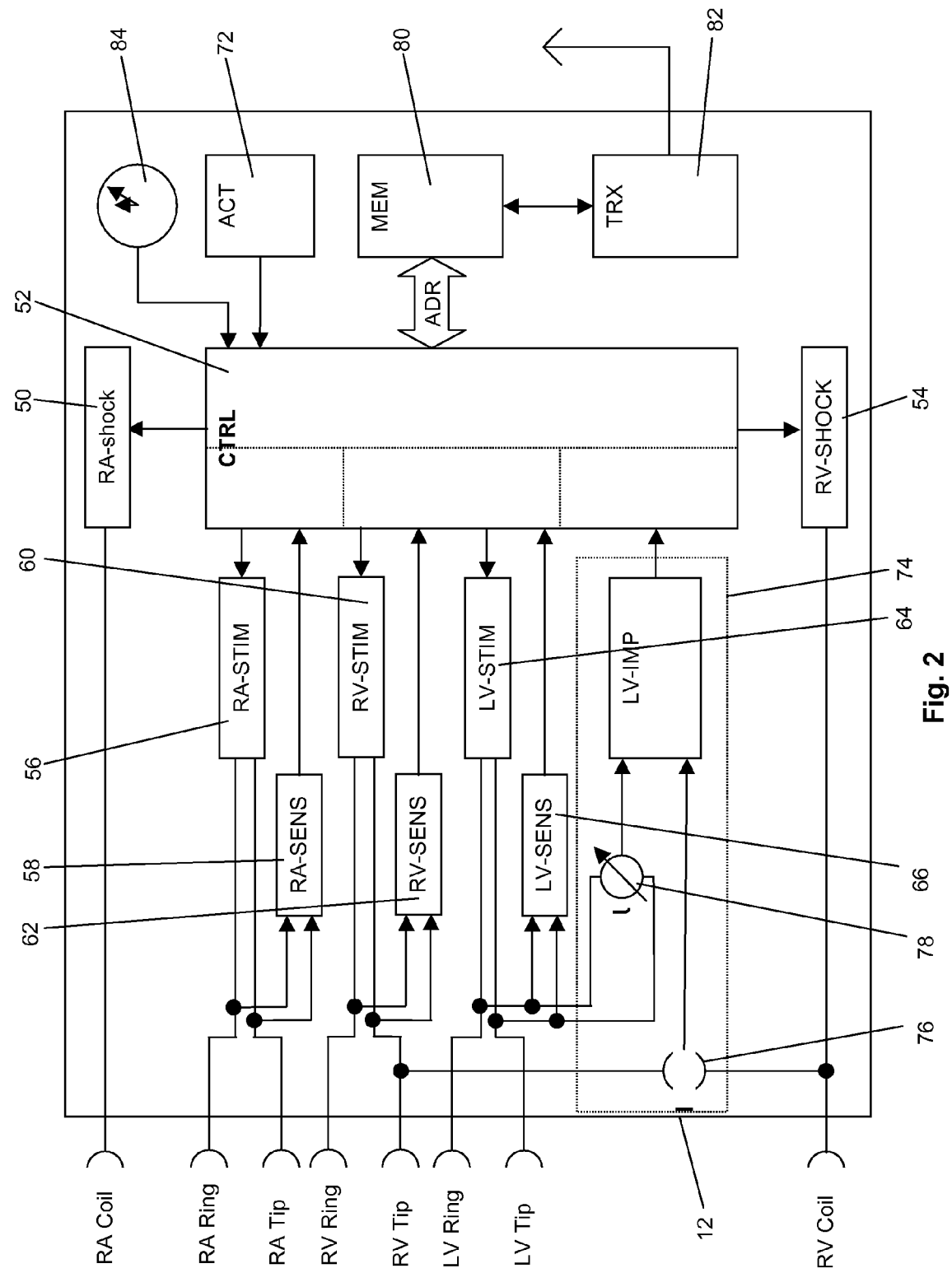
FIG. 2 shows a schematic block diagram of the heart stimulator of FIG. 1.

Right atrial shock coil 40 is connected to right atrial shock generator 50 (see FIG. 2) that is controlled by a control unit 52 of heart stimulator 10.

Similarly, right ventricular shock coil 36 is connected to a right ventricular shock generator 54 that is also connected to control unit 52.

Right atrial tip electrode 28 and right atrial ring electrode 30 are both connected to a right atrial stimulation pulse generator 56 and a right atrial sensing stage 58 that are internally both connected to control unit 52.

Right atrial stimulation pulse generator 56 is adapted to generate atrial stimulation pulses of sufficient strength to cause an excitation of atrial myocardium by an electrical pulse delivered via right atrial tip electrode 28 and right atrial ring electrode 30. Preferably, means are provided to adapt the right atrial stimulation pulse strength to the stimulation threshold in the right atrium.

Right atrial sensing stage 58 is adapted to pick up myocardial potentials indicating an intrinsic atrial excitation that corresponds to a natural atrial contraction. By way of right atrial sensing stage 58, it is possible to stimulate the right atrium 42 of heart 22 in a demand mode wherein a right atrial stimulation pulse is inhibited if an intrinsic atrial event (intrinsic atrial excitation) is sensed by right atrial sensing stage 58 prior to expiration of an atrial escape interval.

In a similar manner, right ventricular ring electrode 34 and right ventricular tip electrode 32 are connected to right ventricular stimulation pulse generator 60 and to a right ventricular sensing stage 62 that in turn are connected to control unit 52. By way of right ventricular tip electrode 32, right ventricular ring electrode 34, right ventricular stimulation generator 60 and right ventricular sensing stage 62, right ventricular stimulation pulses can be delivered in a demand mode to the right ventricle 38 of heart 22.

In the same way left ventricular tip electrode 32 and left ventricular ring electrode 26 are connected to the left ventricular stimulation pulse generator 64 and the left ventricular sensing stage 66 that internal connected to control unit 52 and that allow for stimulating a left ventricle 70 of heart 22.

Triggering and inhibition of delivery of stimulation pulses to the right atrium, the right ventricle or the left ventricle is controlled by control unit 52, in a manner known to the man skilled in the art. The timing that schedules delivery of stimulation pulses if needed is controlled by a number of intervals that at least partly may depend on a hemodynamic demand of a patient that is sensed by means of an activity sensor 72 that is connected to control unit 52. Activity sensor 72 allows for rate adaptive pacing wherein a pacing rate (the rate of consecutive ventricular stimulation pulses for a duration of consecutive atrial stimulation pulses) depends on a physiological demand of a patient that is sensed by a way of activity sensor 72. Details of rate adaptation are known to the man skilled in the art but need not to be explained in detail in this description.

Whereas an actual stimulation rate determines the timing from one (paced) heart cycle to another, intervals like the atrioventricular delay interval and the interventricular delay interval determine the timing within one heart cycle. Starting with an atrial event, the right ventricle would be excited (either intrinsically or paced) at the end of the atrioventricular delay interval. A left ventricular contraction should follow the right ventricular contraction at the end of the interventricular delay interval. This shall include the case, wherein the right ventricle and the left ventricle are excited at the same time resulting in an interventricular delay interval duration of zero. Also, it is possible that the left ventricle is excited prior to the right ventricle resulting in a negative interventricular delay interval duration.

In any case, the atrial ventricular delay interval duration and the interventricular delay interval duration need to be adapted to an individual heart in order to achieve an optimized cardiac output.

Heart stimulator 10 is adapted to determine an optimal atrioventricular delay interval AVD and an optimal interventricular delay interval VVD automatically. This is achieved by finding that atrioventricular delay interval AVD and that interventricular delay interval VVD that leads to minimum mechanical asynchrony between the right ventricular contraction and the corresponding left ventricular contraction.

Further, heart stimulator 10 is adapted to apply different delay interval, AVD and VVD, for daytime and nighttime. The $AVD_{day}$ to be applied during daytime may correspond to the optimized AVD as mentioned above. Likewise the $VVD_{day}$ to be applied during daytime may correspond to the optimized AVD as mentioned above.

During night time, these delay intervals are adapted as follows:

$$AVD_{night} = AVD_{day} + \Delta AVD$$

$$VVD_{night} = VVD_{day} + \Delta VVD$$

In order to enable control unit CTRL 40 to determine when to a apply daytime delays and when to apply nighttime delays, a clock 84 is provided that is connected to the control unit. Further, memory 80 contains data defining daytime and nighttime with respect to clock 80 and thus enables control unit 40 to adapt AVD and VVD according to the data contained in memory 80 and an output signal of clock 84.

The heart stimulator is adapted to automatically determine rest (nighttime) and active (daytime) phases based on analysis of the signal measured by activity sensor as disclosed in U.S. Pat. No. 5,300,092 and U.S. Pat. No. 5,350,408 patents, or based on the analysis of the respiration signal measured by impedance sensor as disclosed in U.S. Pat. No. 6,519,494 patent, all incorporated herein by reference. The time data thus determined is stored in memory 80.

Memory 80 further comprises bins (not displayed) for statistical data received or generated by control unit 40. Separate bins for daytime statistical data and nighttime statistical data are provided. Control unit 40 is adapted to store the statistical data in one of said bins depending on whether said control unit receives these data during daytime or nighttime.

Memory 80 is connected to a telemetry unit TRX 82 that serves for wireless transmission of data to an external device (not shown). The external device has a telemetry unit matching the heart stimulator's telemetry unit 82. The external device can be a programmer that further comprises a display and is adapted to display a user-interface through which a user can select display of daily (day plus night) lumped statistics, or daytime statistics only, or nighttime statistics only.

Although an exemplary embodiment of the present invention has been shown and described, it should be apparent to those of ordinary skill that a number of changes and modifications to the invention may be made without departing from the spirit and scope of the invention. This invention can readily be adapted to such devices by following the present teachings. All such changes, modifications and alterations should therefore be recognized as falling within the scope of the present invention.

What is claimed is:

1. A heart stimulator for pacing of a heart, comprising:
   stimulation electrode leads;
   at least one stimulation pulse generator being connected to or being connectable to the stimulation electrode leads that are configured to stimulate at least two different chambers of a heart, wherein said stimulation pulse generator is configured to generate stimulation pulses to pace an individual heart chamber when triggered;
   a control unit, connected to said at least one stimulation pulse generator and configured to trigger the stimulation pulses for the individual heart chamber such that a stimulation of a next heart chamber occurs when an intra heart cycle delay interval started by natural or a stimulated contraction of a previous heart chamber expires; and, wherein said intra heart cycle delay interval $D_{night}$ during night time differs from a corresponding intra heart cycle delay interval $D_{day}$ to be applied during day time by a preset difference interval DD: $D_{night}=D_{day}+\Delta D$;
wherein said control unit is further configured to nighttime adaptation of AVD and in operation modes including specially designed short AVD settings; and,
wherein said control unit is further configured to
   inhibit nighttime adaptation of AVD during a right ventricle automatic capture control RV-ACC, or
   inhibit said nighttime adaptation of AVD during rhythm-based automatic right atrial threshold tracking RA-ATT, or
   inhibit said nighttime adaptation of AVD when a negative AV hysteresis is activated.

2. The heart stimulator according to claim 1, comprising:
said at least one stimulation pulse generator comprising a right atrial stimulation pulse generator and a right ventricular stimulation pulse generator that can be triggered separately by said control unit;
wherein said intra heart cycle delay interval is an atrioventricular interval AVD that is started by a right atrial event RA and that schedules a right ventricular stimulation pulse RVp to be delivered at expiration of said AVD unless inhibited; and,
wherein said control unit is configured to apply a daytime $AVD_{day}$ at daytime and a nighttime $AVD_{night}$ at night that differ from each other by an offset interval $\Delta AVD$ as follows: $AVD_{night}=AVD_{day}+\Delta AVD$.

3. The heart stimulator according to claim 1, comprising:
said at least one stimulation pulse generator comprising a right ventricular stimulation pulse generator and a left ventricular stimulation pulse generator that can be triggered separately by said control unit;
wherein said intra heart cycle delay interval is an interventricular interval VVD that is started by a right ventricular event RV and that schedules a left ventricular stimulation pulse LVp to be delivered at expiration of said VVD unless inhibited; and,
wherein said control unit is configured to apply a daytime $VVD_{day}$ at daytime and a nighttime $VVD_{night}$ at night that differ from each other by an offset interval $\Delta VVD$ as follows: $VVD_{night}=VVD_{day}+\Delta VVD$.

4. The heart stimulator according to claim 2, wherein said control unit is configured to adjust said AVD with heart rate, and to set said nighttime $AVD_{night}$ to be a sum of said daytime $AVD_{day}$ that is dynamic and that varies with said heart rate and said $\Delta AVD$ that also adjusts with said heart rate.

5. The heart stimulator according to claim 1, wherein said control unit is configured to switch between a short AVD and a long hysteresis AVD, and to adapt said nighttime $AVD_{night}$ by adding $\Delta AVD$ to said short AVD and said long AVD, respectively.

6. The heart stimulator according to claim 1, wherein said control unit is connected to a clock and a memory that contains data that defines daytime and nighttime with respect to said clock and wherein said control unit is adapts AVD based on said data contained in said memory and an output signal of said clock.

7. The heart stimulator according to claim 6, wherein said control unit is configured to automatically determine said data to be stored in said memory based on analysis of a signal measured by an activity sensor or based on an analysis of a respiration signal measured by an impedance sensor.

8. The heart stimulator according to claim 1, wherein said control unit is connected to a statistics memory comprising separate bins for daytime statistical data and nighttime statistical data and wherein said control unit is configured to store statistical data in one of said separate bins depending on whether said control unit receives data during daytime or nighttime.

9. The heart stimulator according to claim 1, wherein said control unit is configured to collect one or more of the following statistical data separately for daytime and nighttime:
   event sequence counters AS-VS, AS-VP, AP-VS, AP-VP, ectopic event counters AES, VES,
   unused event counters Ars in PVARP, far-field As, Vrs,
   detection counters AT/AF, VT/VF, PMT, VES lock in, 2:1 lock in,
   therapy counters mode switch, ATP, cardioversion/defibrillation,
   trend histograms A/V rate, A/V amplitude, impedance, activity sensor,
   pacing parameters VP percentage, AP/VP amplitude, atrial/ventricle threshold,
   measured or derived diagnostic parameters heart rate variability, body temperature, blood pressure, transthoracic impedance.

10. The heart stimulator according to claim 9 further comprising a programmer, wherein said heart stimulator comprises a memory for statistical data and a telemetry unit for wireless communication of the statistical data and wherein the programmer comprises a programmer's telemetry unit and a display and is configured to display a user-interface through which a user can select display of daily, day plus night, lumped statistics, or daytime statistics only, or nighttime statistics only.

11. A heart stimulator for pacing of a heart, comprising:
stimulation electrode leads;
at least one stimulation pulse generator being connected to or being connectable to the stimulation electrode leads that are configured to stimulate at least two different chambers of a heart, wherein said stimulation pulse generator is configured to generate stimulation pulses to pace an individual heart chamber when triggered;
a control unit, connected to said at least one stimulation pulse generator and configured to trigger the stimulation pulses for the individual heart chamber such that a stimulation of a next heart chamber occurs when an intra heart cycle delay interval started by natural or a stimulated contraction of a previous heart chamber expires;
wherein said intra heart cycle delay interval $D_{night}$ during night time differs from a corresponding intra heart cycle delay interval $D_{day}$ to be applied during day time by a preset difference interval DD: $D_{night}=D_{day}+\Delta D$; and,
wherein said control unit is further configured to apply different daytime AVDs depending on whether the event starting the AVD is a sense event or a pace event and thus to apply a sensed AVD and paced AVD with programmed sense compensation wherein the control unit is further configured to set the nighttime sense $AVD_{night}$ to be said daytime sense $AVD_{day}$ plus $\Delta AVD$, and said nighttime pace $AVD_{night}$ to be said daytime pace $AVD_{day}$ plus $\Delta AVD$.

12. A heart stimulator for pacing of a heart, comprising:
stimulation electrode leads;
at least one stimulation pulse generator being connected to or being connectable to the stimulation electrode leads that are configured to stimulate at least two different chambers of a heart, wherein said stimulation pulse generator is configured to generate stimulation pulses to pace an individual heart chamber when triggered;
a control unit, connected to said at least one stimulation pulse generator and configured to trigger the stimulation pulses for the individual heart chamber such that a stimulation of a next heart chamber occurs when an intra heart cycle delay interval started by natural or a stimulated contraction of a previous heart chamber expires;

wherein said intra heart cycle delay interval $D_{night}$ during night time differs from a corresponding intra heart cycle delay interval $D_{day}$ to be applied during day time by a preset difference interval DD: $D_{night}=D_{day}+AD$;

wherein said control unit is further configured to inhibit nighttime adaptation of AVD and in operation modes including specially designed short AVD settings; and, wherein said control unit is further configured to
- inhibit nighttime adaptation of AVD during a right ventricle automatic capture control RV-ACC, or
- inhibit said nighttime adaptation of AVD during rhythm-based automatic right atrial threshold tracking RA-ATT, or
- inhibit said nighttime adaptation of AVD when a negative AV hysteresis is activated.

* * * * *